United States Patent
Syvret et al.

(10) Patent No.: US 10,590,150 B2
(45) Date of Patent: Mar. 17, 2020

(54) PREPARATION OF FLUOROSILICON COMPOUNDS

(71) Applicant: Arkema Inc., King of Prussia, PA (US)

(72) Inventors: Robert George Syvret, Allentown, PA (US); Craig Alan Polsz, Newtown, PA (US)

(73) Assignee: Arkema Inc., King of Prussia, PA (US)

( * ) Notice: Subject to any disclaimer, the term of this patent is extended or adjusted under 35 U.S.C. 154(b) by 0 days.

(21) Appl. No.: 16/057,886

(22) Filed: Aug. 8, 2018

(65) Prior Publication Data

US 2018/0346492 A1  Dec. 6, 2018

Related U.S. Application Data

(62) Division of application No. 15/506,322, filed as application No. PCT/US2015/045168 on Aug. 14, 2015, now abandoned.

(60) Provisional application No. 62/042,296, filed on Aug. 27, 2014.

(51) Int. Cl.
*C07F 7/14* (2006.01)
*C07F 7/12* (2006.01)

(52) U.S. Cl.
CPC .......... *C07F 7/14* (2013.01); *C07F 7/12* (2013.01); *C07F 7/122* (2013.01); *C07F 7/123* (2013.01); *C07F 7/125* (2013.01)

(58) Field of Classification Search
None
See application file for complete search history.

(56) References Cited

U.S. PATENT DOCUMENTS

| | | | |
|---|---|---|---|
| 2,658,908 A | 11/1953 | Nitzsche et al. | |
| 3,053,874 A | 9/1962 | Kenmore et al. | |
| 3,696,150 A | 10/1972 | Lichstein et al. | |
| 3,948,973 A | 4/1976 | Phillips | |
| 4,053,530 A | 10/1977 | Schindel | |
| 4,690,997 A | 9/1987 | Cella et al. | |
| 4,730,073 A | 3/1988 | Takago et al. | |
| 5,629,439 A | 5/1997 | Bank et al. | |
| 5,756,795 A | 5/1998 | Bank et al. | |
| 5,756,796 A | 5/1998 | Davern et al. | |
| 5,773,507 A | 6/1998 | Incorvia et al. | |
| 2007/0065728 A1 | 3/2007 | Zhang et al. | |
| 2011/0266490 A1 | 11/2011 | West et al. | |
| 2012/0315536 A1 | 12/2012 | Bhat et al. | |

FOREIGN PATENT DOCUMENTS

WO  WO 94/14821  7/1994

OTHER PUBLICATIONS

Borisov et al. (in "Organosilicon compounds of Group III elements", Ch. 3), Organosilicon. Heteropolymers and Heterocompounds, © Plenum Press, New York 1970. (Year: 1970).*
Emeleus et al., J. Chem. Soc., 1958, 604-609. (Year: 1958).*
Tianqiao Yong., et al; Journal of Power Sources, Elsevier, 254 (2014), pp. 29-32, "Organosilicon compounds containing nitrile and oligo(ethylene oxide) substituents as safe electrolytes for high-voltage lithium-ion batteries".
U.S. National Library of Medicine—National Center for Biotechnology Information; PubChem—Open Chemistry Data Base—Compound Summary for CID 14479 (3-Cyanopropyl)methyldichlorosilane Modified Date Aug. 5, 2015; Create Date Mar. 27, 2005; 13 Pages.
U.S. National Library of Medicine—National Center for Biotechnology Information; PubChem—Open Chemistry Data Base—Compound Summary for CID 22079074 AGN-PC-03JZO2 Nov. 5, 2014; pp. 1-11.
U.S. National Library of Medicine—National Center for Biotechnology Information; PubChem—Open Chemistry Data Base—Compound Summary for CID 57848168 AGN-PC-0BYK7O Nov. 5, 2014; pp. 1-11.
U.S. National Library of Medicine—National Center for Biotechnology Information; PubChem—Open Chemistry Data Base—Compound Summary for CID 4589186 3-trimethylsilyloxypropanenitrile Nov. 5, 2014; pp. 1-12.
Borisov, SN.,et al; Organosilicon Compounds of Group III Elements; Chapter 3, Organolilicon Herteropolymers and Heterocompounds; Plenum Press, New York 1970; pp. 169-200.
Bioconjugate Chem. 1999, 10, pp. 346-353; Falipou et al, "New Use of Cyanosilane Coupling Agent for Direct Binding of Antibodies to Silica Supports Physicochemical Characterization of Molecularly Bioengineered Layers".
The Reaction of Methyldisiloxanes and 1:1-Dimethyl-disilthiane with Boroan and Hydrogen Halides. Emeleus and Onyszchuk; Sep. 27, 1957 pp. 604-609.
Journal of Organometallic Chemistry, 87 (1975) pp. 137-143; Elsevier Sequoia S. A., Lausanne—Printed in The Netherlands; "The Interaction of Organosilanes with Triphenylmethyl Tetrafluoroborate"; Bulkowski et al Dept. of Chemistry, Carnegie-Mellon University, Pittsburg, PA 15213 (USA).
Borisov et al. (in "Organosilicon compounds of Group III elements", ch 3), Organosilicon. Heteropolymers and Heterocompounds, © Plenum Press, New York 1970.

* cited by examiner

*Primary Examiner* — Clinton A Brooks
*Assistant Examiner* — Kofi Adzamli
(74) *Attorney, Agent, or Firm* — Steven D. Boyd

(57) ABSTRACT

Methods of synthesizing fluorosilanes containing cyano-substituted alkyl groups are provided. For example, 3-cyanopropyldimethylfluorosilane may be produced by reacting tetramethyldisiloxane and boron trifluoride to obtain fluorodimethylsilane and then reacting the fluorodimethylsilane with allyl cyanide, in the presence of a hydrosilylation catalyst.

7 Claims, No Drawings

PREPARATION OF FLUOROSILICON COMPOUNDS

This present application is a divisional application of U.S. application Ser. No. 15/506,322 filed Feb. 24, 2017 which is the national phase under 35 USC § 371 of prior PCT International Application Number PCT/US2015/045168 filed Aug. 14, 2015 which designated the United States of America and claimed priority to U.S. Provisional Patent Application Ser. No. 62/042,296 filed Aug. 27, 2014.

FIELD OF THE INVENTION

The present invention pertains to methods for synthesizing fluorosilicon compounds such as cyanoalkyldifluoromethyisilanes and cyanoalkyldimethylfluorosilanes.

DISCUSSION OF THE RELATED ART

Fluorosilicon compounds such as cyanoalkyldifluoromethylsilanes and cyanoalkyldimethylfluorosilanes are useful in various applications such as battery fabrication, semiconductor deposition, fluorosilicone glass formation, and semiconductor etching agents. The development of economically viable and industrially practical methods for synthesizing such compounds would therefore be of great interest.

BRIEF SUMMARY OF THE INVENTION

One aspect of the invention provides a method of making 3-cyanopropyldimethylfluorosilane, comprising:
  a) reacting tetramethyldisiloxane and boron trifluoride to obtain fluorodimethylsilane; and
  b) reacting fluorodimethylsilane obtained in step a) with allyl cyanide.

The reaction of fluorodimethylsilane and allyl cyanide may be carried out in the presence of a hydrosilylation catalyst, such as an organoplatinum coordination complex (e.g., Karstedt's catalyst).

Also provided by the invention is a method of making 3-cyanopropyldimethylfluorosilane comprising a step of reacting bis(3-cyanopropyl)tetramethyldisiloxane and boron trifluoride. The boron trifluoride may be in the form of a Lewis base complex, such as an etherate complex.

Yet another aspect of the invention furnishes a method of making 3-cyanopropyldifluoromethylsilane comprising a step of reacting allyl cyanide and difluoromethylsilane. The difluoromethylsilane may be prepared by reacting a cyclic siloxane containing silicon atoms bearing hydrogen and methyl substituents (e.g., 2,4,6,8-tetramethylcyclotetrasiloxane) with boron trifluoride. The reaction of allyl cyanide and difluoromethylsilane may be catalyzed using a hydrosilylation catalyst.

In another aspect, the invention provides a method of making a cyanoalkyldifluoromethylsilane (e.g., 3-cyanopropyldifluooromethylsilane or 2-cyanoethyldifluoromethylsilane), comprising a step of reacting a cyanoalkyldichloromethylsilane with ammonium bifluoride.

The above-described reactions may be conducted in the presence of a solvent, in particular an inert organic solvent such as toluene, that forms an azeotrope with water. Removal of water from the compound that is the desired synthetic target is facilitated, since such solvent permits any residual water which may be present in the reaction product mixture to be separated by azeotropic distillation with the solvent.

DETAILED DESCRIPTION OF CERTAIN EMBODIMENTS OF THE INVENTION

Synthesis of 3-cyanopropyldimethylfluorosilane

The compound 3-cyanopropyldimethylfluorosilane (sometimes referred to herein as "F1S$_3$MN") has the chemical structure NCCH$_2$CH$_2$CH$_2$Si(CH$_3$)$_2$F and thus has a cyanopropyl group, two methyl groups and a fluorine atom bonded to a silicon atom.

In one aspect of the invention, F1S$_3$MN is prepared by first synthesizing fluorodimethylsilane [HSiF(CH$_3$)$_2$] by reacting tetramethyldisiloxane [(H$_3$C)$_2$Si—O—Si(CH$_3$)$_2$] with boron trifluoride (BF$_3$), which acts as a fluorinating agent, to yield fluorodimethylsilane and then reacting the fluorodimethylsilane thereby obtained with allyl cyanide (H$_2$C=CH—CH$_2$—CN). The boron trifluoride may be supplied in any suitable form, including in neat or solvated form. In one aspect of the invention, a Lewis base complex of BF$_3$ is employed, such as an etherate complex. For example, boron trifluoride diethyl etherate (BF$_3$.OEt$_2$) may be utilized. The stoichiometry of BF$_3$ to tetramethyldisiloxane may be varied and optimized using standard experimental procedures, but typically the molar ratio of BF$_3$ to tetramethyldisiloxane is advantageously within the range of from about 0.3:1 to about 1:1. Procedures for reacting tetramethyldisiloxane and boron trifluoride diethyl etherate are known in the art and may be readily adapted for use in the present invention (see, for example, J. Chem. Soc., 1958, pages 604-609, the disclosure of which is incorporated herein by reference in its entirety for all purposes). In one embodiment of the invention, the boron trifluoride is added to a solution of the tetramethyldisiloxane in an inert solvent such as an aromatic hydrocarbon. The solvent may be a solvent such as toluene that is capable of forming an azeotrope with water. The use of such a solvent is advantageous since it permits removal of water from the reaction product as an azeotrope with the solvent, thereby leading to an isolated F1S$_3$MN product having a very low water content, which is highly desirable. The reaction mixture may be maintained at a temperature effective to achieve the desired reaction of the starting material to selectively yield the desired fluorodimethylsilane within a practicably short period of time. For example, reaction temperatures of from about 30° C. to about 100° C. and reaction times of from about 1 to about 10 hours may be employed. The desired product, fluorodimethylsilane, is relatively volatile and thus may be recovered from the reaction mixture by methods such as distillation.

The next step of the above-mentioned method involves reacting the fluorodimethylsilane with allyl cyanide. Generally speaking, it will be advantageous to employ roughly equimolar amounts of the two reactants. The molar ratio of fluorodimethylsilane to allyl cyanide may be from about 0.7:1 to about 1.3:1, for example. In one embodiment of the invention, the reaction is carried out in the presence of a hydrosilylation catalyst, in particular a platinum-containing catalyst such as an organoplatinum coordination complex having activity as a hydrosilylation catalyst. Karstedt's catalyst, which is an organoplatinum compound derived from divinyl-containing disiloxane (by treatment of chloroplatinic acid with divinyltetramethyldisiloxane), is an example of a suitable catalyst for this purpose. Other suitable hydrosilylation catalysts include, for example, Wilkinson's catalyst (tris(triphenylphosphine)rhodium (I) chloride), the cobalt carbonyl complex Co$_2$(CO)$_8$, and H$_2$PtCl$_6$ (Speier's catalyst). The fluorodimethylsilane and allyl cyanide are reacted for a time and at a temperature effective to provide the desired product 3-cyanopropyldimethylfluorosilane. For example, the allyl cyanide may be charged to a suitable reaction vessel, optionally together with one or more inert solvents such as an aromatic hydrocarbon (preferably a solvent such as toluene that is capable of forming an azeotrope with water, thereby permitting the removal of water from the reaction product as a toluene/water azeotrope) and/or a hydrosilylation catalyst. The fluorodimethylsilane may then be added to and combined with the contents of the reaction vessel. The addition of the fluorodimethylsilane may be carried out in stages. For example, a first portion of the fluorodimethylsilane may be added (optionally, in an incremental fashion) and the resulting mixture then permitted to react for a period of time before adding a second portion of the fluorodimethylsilane. The reaction mixture may be maintained, for example, at a temperature of from about 70° C. to about 120° C. Once the reaction has been carried out to the desired degree of completion, the desired product, 3-cyanopropyldimethylfluorosilane, may be recovered from the reaction product mixture and purified by any suitable method, such as fractional distillation or the like. As previously mentioned, residual water may be removed by azeotropic distillation from the reaction product, if a solvent such as toluene is present which is capable of forming an azeotrope with water.

In another aspect of the invention, 3-cyanopropyldimethylfluorosilane is prepared by a process comprising a step of reacting bis(3-cyanopropyl)tetramethyldisiloxane and boron trifluoride. Bis(3-cyanopropyl)tetramethyldisiloxane [NCCH$_2$CH$_2$CH$_2$(CH$_3$)$_2$SiOSi(CH$_3$)$_2$CH$_2$CH$_2$CH$_2$CN] is available commercially and may be prepared by known synthetic methods. As explained above in connection with a further aspect of the invention, the boron trifluoride may be in the form of a Lewis base complex, such as an etherate complex. The boron trifluoride may be added to a solution of the bis(cyanopropyl)tetramethyldisiloxane in an organic solvent (e.g., an aromatic hydrocarbon such as toluene, in particular a solvent capable of forming an azeotrope with water to assist in removing residual water from the reaction product). The stoichiometry of bis(3-cyanopropyl)tetramethyldisiloxane to BF$_3$ may be varied as may be desired in order to optimize the yield of the desired 3-cyanopropyldimethylfluorosilane, but typically the molar ratio of bis(3-cyanopropyl)tetramethyldisiloxane to boron trifluoride will be from about 0.3:1 to about 1:1. The mixture may be heated for a time and at a temperature effective to achieve fluorination and conversion of the bis(3-cyanopropyl)tetramethyldisiloxane to 3-cyanopropyldimethylfluorosilane. For example, reaction temperatures of from about 60° C. to about 100° C. and reaction times of from about 1 hour to about 6 hours may be utilized. Once the desired degree of conversion has been achieved, the 3-cyanopropyldimethylfluorosilane may be recovered from the reaction product mixture by conventional purification methods such as washing the reaction product with aqueous acid and then fractionally distilling the organic layer. If a solvent such as toluene which is capable of forming an azeotrope with water is present, a fore-cut containing residual water (as an azeotrope with solvent) may be first collected before distilling the desired 3-cyanopropyldimethylfluorosilane, thereby reducing the water content of the recovered 3-cyanopropyldimethylfluorosilane.

Synthesis of Cyanoalkyldifluoromethylsilanes

A method of making 3-cyanopropyldifluoromethylsilane in accordance with the present invention comprises a step of reacting allyl cyanide and difluoromethylsilane [HSi(CH$_3$)F$_2$]. The difluoromethylsilane may be obtained by carrying out an initial step of reacting a cyclic siloxane containing Si atoms bearing hydrogen and methyl substituents (e.g., 2,4,6-trimethylcyclotrisiloxane; 2,4,6,8-tetramethylcyclotetrasiloxane, 2,4,6,8,10-pentamethylcyclopentasiloxane; 2,4,6,8,10,12-hexamethylcyclohexasiloxane; and higher homologues) and boron trifluoride. Thus, the cyclic siloxane contains repeating units having the structure [—O—SiH(CH$_3$)—]. Mixtures of such cyclic siloxanes may be employed as a starting material. The synthesis of difluoromethylsilane using such a reaction has not been previously reported and thus is considered to be an additional aspect of the present invention. The boron trifluoride may be in the form of a Lewis base complex, such as an etherate complex (e.g., boron trifluoride diethyl ether). The siloxane starting materials such as 2,4,6,8-tetramethylcyclotetrasiloxane are known compounds and may be readily obtained from commercial sources or prepared by conventional synthetic methods. One suitable procedure for reacting a cyclic siloxane such as 2,4,6,8-tetramethylcyclotetrasiloxane and BF$_3$ involves charging a mixture of 2,4,6,8-tetramethylcyclotetrasiloxane and an organic solvent such as an aromatic hydrocarbon (e.g., toluene) to a reaction vessel and then adding the BF$_3$ (e.g., in the form of boron trifluoride diethyl ether) incrementally to the contents of the reaction vessel, with agitation (stirring). The organic solvent may be selected to be one that is capable of forming an azeotrope with water. Typically, from about 0.5 to about 1 mole BF$_3$ per mole of Si in the cyclic siloxane is utilized in the reaction. For example, from about 2 to about 4 moles of BF$_3$ per mole of 2,4,6,8-tetramethylcyclotetrasiloxane may be used. The resulting reaction mixture may be heated at a temperature effective to achieve the desired reaction to provide difluoromethylsilane (e.g., about 50° C. to about 100° C.). The difluoromethylsilane may then be isolated or separated from the reaction product using any suitable method such as distillation, then further reacted with allyl cyanide. The difluoromethylsilane and allyl cyanide are combined and heated for a time and at a temperature effective to achieve the desired reaction to provide 3-cyanopropyldifluoromethylsilane [NCCH$_2$CH$_2$CH$_2$Si(CH$_3$)F$_2$]. A hydrosilylation catalyst such as, for example, Karstedt's catalyst, Wilkinson's catalyst (tris(triphenylphosphine)rhodium (I) chloride), the cobalt carbonyl complex Co$_2$(CO)$_8$, or H$_2$PtCl$_6$ (Speier's catalyst) may additionally be present to accelerate the rate of reaction. For example, allyl cyanide and a hydrosilylation catalyst such as Karstedt's catalyst may be introduced into a reaction vessel and heated to the desired reaction temperature (e.g., about 70° C. to about 110° C.). The difluoromethylsilane is then introduced into the reaction vessel, with such introduction being carried out incrementally or portion-wise. Additional amounts of hydrosilylation catalyst may be introduced during the course of the reaction. The molar ratio of allyl cyanide to difluoromethylsilane may suitably be from about 0.7:1 to about 1.3:1, for example. Once the reaction has been carried out to the desired level of completion, the desired 3-cyanopropyldifluoromethylsilane may be recovered from the reaction product by any suitable method, such as distillation. If a solvent such as toluene is present in the reaction product mixture that is capable of forming an azeotrope with water, a water/solvent azeotrope may first be removed by distillation, thereby reducing the water content of the 3-cyanopropyldifluoromethylsilane subsequently recovered by distillation.

The present invention further provides, in one aspect, a method of making a cyanoalkyldifluoromethylsilane, comprising a step of reacting a cyanoalkyldichloromethylsilane with ammonium bifluoride. Suitable cyanoalkyldichloromethylsilanes contain, as substituents on the silicon atom, a cyanoalkyl group (such as 2-cyanoethyl or 3-cyanopropyl), two chlorine atoms and a methyl group. The cyanoalkyldichloromethylsilane may, for example, be selected from the group consisting of 3-cyanopropyldichloromethylsilane [$NCCH_2CH_2CH_2Si(CH_3)(Cl)_2$] and 2-cyanoethyldichloromethylsilane [$NCCH_2CH_2Si(CH_3)(Cl)_2$]. Such compounds are known in the art and may be prepared by adaptation of synthetic methods such as reaction of dichloromethylsilane with acrylonitrile or 3-butene nitrile. Such reaction may be a hydrosilylation reaction catalyzed by a suitable catalyst, such as a copper-based hydrosilylation catalyst. The chlorine atoms in the starting cyanoalkyldichloromethylsilane are replaced by fluorine atoms as a result of the reaction with ammonium bifluoride, thereby yielding the cyanoalkyldifluoromethylsilane. For example, 3-cyanopropyldichloromethylsilane [$NCCH_2CH_2CH_2Si(CH_3)(Cl)_2$] is converted to 3-cyanopropyldifluoromethylsilane [$NCCH_2CH_2CH_2Si(CH_3)(F)_2$] and 2-cyanoethyldichloromethylsilane [$NCCH_2CH_2Si(CH_3)(Cl)_2$] is converted to 2-cyanoethyldifluoromethylsilane [$NCCH_2CH_2Si(CH_3)(F)_2$].

Ammonium bifluoride is sometimes also referred to as ABF, ammonium hydrogen difluoride, ammonium acid fluoride, $H_4NHF_2$ or $H_4NF.HF$. The fluorination reaction may be carried out by contacting the cyanoalkyldichloromethylsilane with ammonium bifluoride for a time and at a temperature effective to replace the chlorine atoms present in the cyanoalkyldichloromethylsilane with fluorine atoms. For example, a mixture of the cyanoalkyldichloromethylsilane and ammonium bifluoride may be placed in a vessel and heated, with the desired product cyanoalkyldifluoromethylsilane, which has a lower boiling point than the corresponding cyanoalkyldichloromethylsilane, being removed by distillation as it is formed. Typically, about 0.5 to about 1.5 moles of ammonium bifluoride per mole of cyanoalkyldichloromethylsilane is utilized. Reaction temperatures of from about 30° C. to about 100° C. are generally suitable, for example. An inert organic solvent capable of forming an azeotrope with water such as toluene may be present in the reaction product mixture; azeotropic distillation of the reaction product mixture to remove water as an azeotrope with the organic solvent may be employed as a method of reducing the water content of the cyanoalkyldifluoromethylsilane that is recovered from the reaction product mixture. The production of cyanoalkyldifluoromethylsilane having a very low level of water is highly desirable.

Aspects of the present invention including:
1. A method of making 3-cyanopropyldimethylfluorosilane, comprising:
   a) reacting tetramethyldisiloxane and boron trifluoride to obtain fluorodimethylsilane; and
   b) reacting fluorodimethylsilane obtained in step a) with allyl cyanide.
2. The method of claim 1, wherein step b) is carried out in the presence of a hydrosilylation catalyst.
3. The method of any one of claims 1 or 2, wherein fluorodimethylsilane and allyl cyanide are reacted in a molar ratio of from about 0.7:1 to about 1.3:1.
4. The method of any one of the preceding claims, wherein step b) is carried out in the presence of Karstedt's catalyst.
5. The method of any one of the preceding claims, wherein the fluorodimethylsilane and the allyl cyanide are reacted in the presence of a hydrosilylation catalyst at a temperature of from about 70° C. to about 120° C.
6. The method of any one of the preceding claims, wherein step b) is carried out in an inert solvent capable of forming an azeotrope with water.
7. The method of claim 6, wherein the inert solvent is toluene.
8. The method of claims 6 or 7, wherein a reaction product containing 3-cyanopropyldimethylfluorosilane, inert solvent and water is obtained in step b) and the reaction product is subjected to distillation wherein water is removed by azeotropic distillation.
9. The method of any one of the preceding claims, wherein the boron trifluoride is in the form of an etherate complex.
10. A method of making 3-cyanopropyldimethylfluorosilane comprising a step of reacting bis(3-cyanopropyl)tetramethyldisiloxane and boron trifluoride.
11. The method of claim 10, wherein the boron trifluoride is in the form of an etherate complex.
12. The method of any one of claims 10 or 11, wherein the boron trifluoride and the bis(cyanopropyl)tetramethyldisiloxane are reacted at a temperature of from about 60° C. to about 100° C.
13. The method of any one of claims 10, 11 or 12, wherein the boron trifluoride and the bis(cyanopropyl)tetramethyldisiloxane are reacted at a molar ratio of from about 0.3:1 to about 1:1.
14. The method of any one of claims 10, 11, 12 or 13, wherein the reaction is carried out in an inert solvent capable of forming an azeotrope with water.
15. The method of claim 14, wherein the inert solvent is toluene.
16. The method of claims 14 or 15, wherein a reaction product containing 3-cyanopropyldimethylfluorosilane, inert solvent and water is obtained and the reaction product is subjected to distillation wherein water is removed by azeotropic distillation.
17. A method of making 3-cyanopropyldifluoromethylsilane comprising a step of reacting allyl cyanide and difluoromethylsilane.
18. The method of claim 17, additionally comprising an initial step of obtaining the difluoromethylsilane by reacting 2,4,6,8-tetramethylcyclotetrasiloxane and boron trifluoride.
19. The method of any one of claims 17 or 18, wherein the allyl cyanide and difluoromethylsilane are reacted in the presence of a hydrosilylation catalyst at a temperature of from about 70° C. to about 110° C.
20. The method of any one of claims 17, 18 or 19, wherein the allyl cyanide and difluoromethylsilane are reacted in the presence of a hydrosilylation catalyst.
21. The method of claim 20, wherein the hydrosilylation catalyst is Karstedt's catalyst.
22. The method of any one of claims 17 through 21, wherein the allyl cyanide and difluoromethylsilane are reacted at a molar ratio of from about 0.7:1 to about 1.3:1.
23. A method of making a cyanoalkyldifluoromethylsilane, comprising a step of reacting a cyanoalkyldichloromethylsilane with ammonium bifluoride.
24. The method of claim 23, wherein the cyanoalkyldichloromethylsilane is selected from the group consisting of 3-cyanopropyldichloromethylsilane and 2-cyanoethyldichloromethylsilane.
25. The method of claims 23 or 24, wherein the cyanoalkyldichloromethylsilane and ammonium bifluoride are reacted at a molar ratio of from about 0.5 to about 1.5 moles of ammonium bifluoride per mole of cyanoalkyldichloromethylsilane.

26. The method of any one of claims 23, 24 or 25, wherein the reaction is carried out in an inert solvent capable of forming an azeotrope with water.

27. The method of claim 26, wherein the inert solvent is toluene.

28. The method of any one of claims 26 through 27, wherein a reaction product containing cyanoalkyldifluoromethylsilane, inert solvent and water is obtained and the reaction product is subjected to distillation wherein water is removed by azeotropic distillation.

29. A method of making difluoromethylsilane, comprising reacting a cyclic siloxane and boron trifluoride, wherein the cyclic siloxane contains silicon atoms bearing —H and —CH$_3$ groups as substituents.

30. The method of claim 29, wherein the boron trifluoride is in the form of an etherate complex.

31. The method of any one of claims 29 or 30, wherein from about 0.5 to about 1 mole of boron trifluoride per mole of Si present in the cyclic siloxane are reacted.

32. The method of any one of claims 29, 30, or 31, wherein boron trifluoride and the cyclic siloxane are reacted at a temperature of from about 50° C. to about 100° C.

Within this specification embodiments have been described in a way which enables a clear and concise specification to be written, but it is intended and will be appreciated that embodiments may be variously combined or separated without parting from the invention. For example, it will be appreciated that all preferred features described herein are applicable to all aspects of the invention described herein.

EXAMPLES

Example 1: Synthesis of Fluorodimethylsilane (FRMS), FSi(CH$_3$)$_2$H

Using a procedure similar to that described in the prior art (J. Chem. Soc. (1958), page 607), a sample of FDMS was prepared and isolated. Thus, a 500 ml four neck glass flask was equipped with a magnetic stir bar, a ¼" Teflon coated thermocouple connected to a J-Kem controller, an addition funnel with septum secured on top and a dry ice condenser that was connected to the side joint of a Claisen adapter. A second dry ice condenser was connected to the top of the Claisen adapter. The second dry ice condenser was connected to a nitrogen line. The bottom of the Claisen adapter was connected to a two neck 24/40 flask. Rubber septa were placed on the remaining necks of both flasks.

Tetramethyldisiloxane (TMDS), 35.31 g (262.9 mmol) and toluene 101.17 g (1.1 mol) were charged to the four neck flask. Boron trifluoride diethyl etherate (BF$_3$.OEt$_2$), 25.31 g (178.3 mmol) was charged to the addition funnel using a cannula and nitrogen pressure. Dry ice was placed in the first dry ice condenser.

The BF$_3$.OEt$_2$ was added drop-wise to the reaction flask over a 25 minute period. The reaction mixture was then heated from 40 to 90° C. over the course of 4 hours during which the dry ice in the first condenser evaporated and the volatile material was allowed to collect in the second (two neck) flask cooled to dry ice temperature. After no more volatile material was coming over, the collected material was transferred to an evacuated stainless steel cylinder. The collected product fraction was determined to be FDMS by NMR analysis: $\delta^{19}F=-172.31$ ppm; $\delta^1H_q=4.87$ ppm, $^2J(^1H-^{19}F)=57$ Hz; $\delta^1H_{dod}=0.36$ ppm, $^3J(^1H-^{19}F)=6$ Hz and $^3J(^1H-^1H)=3$ Hz.

The collected product was 83 wt. % FDMS and thus the isolated yield based on TMDS was 89%. This FDMS was used directly without purification for the synthesis of 3-cyanopropyldimethylfluorosilane, F1S$_3$MN, according to Example 2 below.

Example 2: Synthesis of 3-cyanopropyldimethylfluorosilane (F1S$_3$MN) by reaction of FDMS with allyl cyanide A 100 ml four-neck 14/20 flask was equipped with a magnetic stir bar, a ¼ Teflon coated thermocouple connected to a J-Kern controller, and a dry ice condenser with outlet going to a nitrogen source. Rubber septa were secured on the remaining two necks. Allyl cyanide 9.57 g (142.6 mmol) and toluene 29.77 g (323.1 mmol) were charged to the reaction flask and heated to 60° C. A ⅛" Teflon line was connected from a cylinder containing fluorodimethylsilane (FDMS) through a rubber septum on the reaction flask. Karstedt's catalyst (0.3 ml) was added to reaction flask and then addition of FDMS was started. The temperature was increased to 90° C. and the FDMS addition was continued at a rate to control reflux in the dry ice condenser. A total of 12.61 g (161.3 mmol) of FDMS was added over six hours after which there was 72% conversion and the reaction was stopped. The next day the reaction mixture was heated to 90° C. and 0.2 ml Karstedt's catalyst was added followed by 2.90 g (37.1 mmol) of FDMS added over one hour. Heating was continued at 90° C. for 3½ hours and then at 100° C. for one hour and then cooled to ambient temperature. Analysis by $^1$H NMR showed absence of allyl cyanide, indicating complete conversion, while $^{19}$F NMR results indicated the desired product had formed. This reaction product was combined with the product from the following paragraph for purification by distillation.

In a similar manner as described above, allyl cyanide 6.59 g (98.2 mmol) was charged to the reaction flask and heated to 90° C. Karstedt's catalyst (0.2 ml) was added to the reaction flask and the addition of FDMS was commenced and continued at a rate to control reflux in the dry ice condenser. A total of 8.40 g (107.5 mmol) of FDMS was added over 2½ hours. The reaction mixture was heated for an additional hour at 100° C. and then cooled to room temperature. Analysis by $^1$H NMR showed the absence of allyl cyanide, indicating complete conversion, and $^{19}$F NMR results indicated the desired product had formed. The reaction mixture was combined with the material described in the previous paragraph and the combined mixture was purified by distillation. After first removing a fore-cut containing toluene, water and other impurities, the desired product F1S$_3$MN was isolated under full vacuum (0.35 torr) at 80° C. Total product recovered was 28.90 g (199.0 mmol) which represents an isolated yield of 83% (based on allyl cyanide). The product composition and purity were confirmed by $^1$H and $^{19}$F NMR analysis: $\delta^{19}F=-163.50$ ppm; $\delta^1H_t=2.39$ ppm; $\delta^1H_m=1.78$ ppm; $\delta^1H_m=0.84$ ppm; $\delta^1H_d=0.25$ ppm, $^3J(^1H-^{19}F)=6$ Hz.

Example 3: Synthesis of 3-cyanopropyldimethylfluorosilane (F1S$_3$MN) by reaction of bis(3-cyanopropyl)tetramethyldisiloxane and BF$_3$ A 250 ml three-neck 14/20 flask was equipped with a magnetic stir bar, a ¼ Teflon coated thermocouple connected to a J-Kem controller, an addition funnel with septum secured on top and a dry ice condenser with outlet going to a nitrogen source. Bis(3-cyanopropyl)tetramethyldisiloxane 31.47 g (130.9 mmol) and toluene 63.10 g (693.5 mmol) were charged to the reaction flask. Boron trifluoride diethyl etherate ($BF_3.OEt_2$) 11.09 g (78.1 mmol) was charged to the addition funnel using a cannula and nitrogen pressure, Dry ice was placed in the dry ice condenser. $BF_3.OEt_2$ was added drop-wise to the reaction flask over 5 minutes and the reaction mixture was then heated to 80° C. for 3½ hours. After the specified time, the reaction mixture was cooled and transferred to a separatory funnel. The reaction mixture was washed with 100 ml of 2-3% aqueous HCl. The layers were separated and the aqueous layer was washed with additional toluene (approx. 50 ml). The organic layers were combined into a 250 ml round bottom flask which was connected to a short path distillation head with water cooled condenser. The flask was heated from 40 to 60° C. under partial vacuum ($\approx$100 torr) and toluene was removed by distillation. After removing toluene, water and other impurities, the remaining product was heated to 40 to 60° C. under full vacuum ($\approx$0.2 torr) and the product was collected. The total product collected was 29.01 g (199.8 mmol) which represents an 85% isolated yield. The identity of the product as $F1S_3MN$ was confirmed by $^1H$ and $^{19}F$ NMR analysis. A portion of the product was analyzed by Karl Fisher technique and determined to contain just 62 ppm $H_2O$ by weight.

Example 4: Synthesis of difluoromethylsilane, DFMS, by reaction of 2,4,6,8-tetramethylcyclotetrasiloxane with $BF_3$ An apparatus and procedure as described in Example 1 was used for Example 4. Thus, 2,4,6,8-tetramethylcyclotetrasiloxane 16.07 g (66.8 mmol) and toluene 100.06 g (1.09 mol) were charged to the four neck flask. Boron trifluoride diethyl etherate ($BF_3.OEt_2$) 26.24 g (184.9 mmol) was charged to the addition funnel. A dry ice/isopropanol slush bath was placed in the second addition funnel and in the bath under the two neck flask. $BF_3.OEt_2$ was added drop-wise to the reaction flask over 25 minutes. No reflux or significant exotherm was observed. The reaction mixture was then heated initially to 60° C., whereupon refluxing commenced, and subsequently further heated to 90° C. The volatile product was collected in the second (two neck) flask and subsequently transferred to a storage cylinder. The collected product fraction was determined to be DFMS by NMR analysis: $\delta^{19}F=-138.50$ ppm; $\delta^1H_r=4.85$ ppm, $^2J$ ($^1H-^{19}F$)=69 Hz; $\delta^1H_{tod}=0.47$ ppm, $^3J$ ($^1H-^{19}F$)=6 Hz; $^3J(^1H-^1H)=3$ Hz. The collected product (22.10 g) was 76 wt. % FDMS and thus the isolated yield was 77%.

Example 5: Synthesis of 3-cyanopropyldifluoromethylsilane, $DFS_3MN$, by reaction of allyl cyanide with DFMS An apparatus and procedure as described in Example 1 was used for Example 5. Thus, a fresh sample of allyl cyanide, 14.00 g (208.7 mmol), prepared via the aqueous reaction between allyl bromide and potassium cyanide, was charged to the reaction flask and heated to 90° C. An ⅛" Teflon® line was connected from a cylinder containing DFMS (prepared according to the procedure provided in Example 4) through a rubber septum and into the reaction flask. Karstedt's catalyst (0.3 ml) was added to reaction flask and the addition of DFMS was initiated and continued at a rate to control the reflux in dry ice condenser. A total of 11.93 g (145.3 mmol) of FDMS was added over six hours. Analysis of the reaction mixture indicated that 55% conversion of the allyl cyanide had been attained. The heating was shut off and the reaction mixture allowed to cool overnight. The next day the reaction mixture was re-heated to 90° C. and 0.2 ml Karstedt's catalyst was added followed by an additional 7.16 g (87.2 mmol) of DFMS over three hours. Analysis of the reaction mixture indicated that 70% conversion of the allyl cyanide had been attained. The heating was shut off and the reaction mixture allowed to cool overnight. After 11 days, the reaction mixture was re-heated to 90° C. and an additional 3.32 g (40.4 mmol) DFMS was added over three hours. Analysis of the reaction mixture indicated complete conversion of allyl cyanide.

The reaction product mixture was distilled under a partial vacuum of 60 torr up to 100° C. to remove toluene, water and other impurities. The product was isolated under full vacuum (0.75 torr) up to 100° C. Total product recovered by distillation was 17.60 g. The product purity was estimated at 80% by NMR analysis. Thus, the isolated yield was about 45%. The product also contained 0.1351% water as determined by Karl Fisher titration.

Example 6: Synthesis of 3-cyanoethyldifluoromethylsilane, $DFS_2MN$, by reaction of $DCS_2MN$ with ammonium bifluoride, ABF A 100 ml four-neck 14/20 flask equipped with a magnetic stirring bar and a water cooled condenser was charged with copper (I) oxide 3.97 g (27.8 mmol) and tetramethylethylenediamine 8.93 g (76.8 mmol). Dichloromethylsilane, DCMS, 23.60 g (205.2 mmol) and acrylonitrile 8.41 g (158.5 mmol) were charged to an addition funnel. The DCMS/acrylonitrile mixture was added to the reaction flask over a 15 minute period and the temperature increased to 60° C. resulting in refluxing in the condenser. After refluxing stopped, heat was applied to continue refluxing up to 90° C. over the next three hours. The product was collected at reduced pressure (0.34 torr) with a pot temperature of 62-65° C. and a head temperature of 41-4° C. Product 3-cyanoethyldichloromethylsilane ($DCS_2MN$), 13.57 g (80.7 mmol), was recovered which represents a 51% yield based on acrylonitrile. The product identification was confirmed by $H^1NMR$.

The product $DCS_2MN$ may be fluorinated, for example using ammonium bifluoride (ABF), to form the desired fluorinated product. $DFS_2MN$. The fluorination reaction may be carried out by contacting the $DCS_2MN$ with ammonium bifluoride for a time and at a temperature effective to replace the chlorine atoms present in the $DCS_2MN$ with fluorine atoms. For example, a mixture of $DCS_2MN$ and ammonium bifluoride may be together in a vessel and the desired product $DFS_2MN$, which has a lower boiling point than $DCS_2MN$, removed by distillation as it is formed. Typically, about 0.5 to about 1.5 moles of ammonium bifluoride per mole of $DCS_2MN$ is utilized. In some cases, it is advantageous to carry out this reaction in an inert solvent capable of forming an azeotrope with water, such as an aromatic hydrocarbon (e.g., toluene). The use of such a solvent permits the effective removal of residual water as a solvent/water azeotrope prior to isolation of the desired $DFS_2MN$ product.

What is claimed is:
1. A method of making 3-cyanopropyldimethylfluorosilane comprising a step of reacting bis(3-cyanopropyl)te- tramethyldisiloxane and boron trifluoride in an inert solvent capable of forming an azeotrope with water.

2. The method of claim 1, wherein the boron trifluoride is in the form of an etherate complex.

3. The method of claim 1, wherein the boron trifluoride and the bis(cyanopropyl)tetramethyldisiloxane are reacted at a temperature of from about 60° C. to about 100° C.

4. The method of claim 1, wherein the boron trifluoride and the bis(cyanopropyl)tetramethyldisiloxane are reacted at a molar ratio of from about 0.3:1 to about 1:1.

5. The method of claim 1, wherein a reaction product containing 3-cyanopropyldimethylfluorosilane, inert solvent and water is obtained and the reaction product is subjected to distillation wherein water is removed by azeotropic distillation.

6. The method of claim 1, wherein the inert solvent is an aromatic hydrocarbon.

7. The method of claim 6, wherein the inert solvent is toluene.

\* \* \* \* \*